(12) United States Patent
Carpenter et al.

(10) Patent No.: US 9,986,750 B2
(45) Date of Patent: *Jun. 5, 2018

(54) ANIMAL FEED COMPOSITIONS AND FEED ADDITIVES

(71) Applicant: BiOWiSH Technologies, Inc., Cincinnati, OH (US)

(72) Inventors: Richard S. Carpenter, West Chester, OH (US); JoElla Barnes, Arcola, IL (US); Michael Stanford Showell, Cincinnati, OH (US)

(73) Assignee: BiOWiSH Technologies Inc., Cincinnati, OH (US)

( * ) Notice: Subject to any disclaimer, the term of this patent is extended or adjusted under 35 U.S.C. 154(b) by 203 days.

This patent is subject to a terminal disclaimer.

(21) Appl. No.: 14/812,598

(22) Filed: Jul. 29, 2015

(65) Prior Publication Data

US 2016/0029666 A1 Feb. 4, 2016

Related U.S. Application Data

(60) Provisional application No. 62/030,460, filed on Jul. 29, 2014, provisional application No. 62/090,756, filed on Dec. 11, 2014.

(51) Int. Cl.
| | | |
|---|---|---|
| *A61K 35/747* | (2015.01) | |
| *A23K 1/00* | (2006.01) | |
| *A61K 35/742* | (2015.01) | |
| *A61K 31/733* | (2006.01) | |
| *A61K 9/16* | (2006.01) | |
| *A23K 40/25* | (2016.01) | |
| *A23K 40/20* | (2016.01) | |
| *A23K 40/30* | (2016.01) | |
| *A23K 10/18* | (2016.01) | |
| *A23K 10/30* | (2016.01) | |

(52) U.S. Cl.
CPC .............. *A23K 1/009* (2013.01); *A23K 10/18* (2016.05); *A23K 10/30* (2016.05); *A23K 40/20* (2016.05); *A23K 40/25* (2016.05); *A23K 40/30* (2016.05); *A61K 9/1664* (2013.01); *A61K 31/733* (2013.01); *A61K 35/742* (2013.01); *A61K 35/747* (2013.01); *A23Y 2220/67* (2013.01); *A23Y 2280/15* (2013.01); *A23Y 2280/55* (2013.01)

(58) Field of Classification Search
CPC ........ A23K 40/20; A23K 40/30; A23K 10/18; A23K 10/30; A23K 1/009; A23Y 2280/55; A23Y 2220/67; A23Y 2280/15; A61K 35/742; A61K 31/733; A61K 9/1664; A61K 35/747

See application file for complete search history.

(56) References Cited

U.S. PATENT DOCUMENTS

| | | | |
|---|---|---|---|
| 8,101,170 B2 | 1/2012 | Plail et al. | |
| 2012/0315249 A1* | 12/2012 | Olmstead | A61K 45/06 424/93.3 |
| 2012/0321592 A1 | 12/2012 | Schmidt et al. | |
| 2013/0330307 A1 | 12/2013 | Millan | |

FOREIGN PATENT DOCUMENTS

| | | | |
|---|---|---|---|
| CN | 102511662 | 6/2012 | |
| RU | 2018313 C1 | 8/1994 | |
| WO | WO-2004043139 A2 * | 5/2004 | ............. A23K 10/16 |
| WO | WO2014/049023 | 4/2014 | |

OTHER PUBLICATIONS

International Search report from corresponding PCT International Application No. PCT/US2015/042656, dated Jan. 7, 2016 received Jan. 13, 2016.

* cited by examiner

*Primary Examiner* — Robert S Cabral (74) *Attorney, Agent, or Firm* — Cooley LLP; Ivor R. Elrifi; Cynthia Kozakiewicz (57) ABSTRACT

The present invention relates to pre-, pro-, and postbiotic compositions and methods of use for improving the health and nutrition of commercial livestock and companion pets.

18 Claims, 3 Drawing Sheets

Figure 3 ations U.S. Ser. No. 62/030,460 filed on Jul. 29,
ANIMAL FEED COMPOSITIONS AND FEED ADDITIVES

RELATED APPLICATIONS

This application claims priority to and benefit of provisional applic 2014 and U.S. Ser. No. 62/090,756 filed on Dec. 11, 2014, the contents of which are herein incorporated by reference in their entirety.

INCORPORATION BY REFERENCE OF SEQUENCE LISTING

The contents of the text file named "BIOW_009001US_SeqList_ST25.txt," which was created on Aug. 18, 2015 and is 3 KB in size, are hereby incorporated by reference in their entirety.

FIELD OF THE INVENTION

The present invention relates to animal feed compositions and feed additives containing a mixture of pre-, pro- and post-biotic materials and their use in promoting animal growth, health, and nutrition.

BACKGROUND OF THE INVENTION

Pre-, Pro-, and post-biotics are relatively new terms used to describe a range of materials that have demonstrated benefits in animal health and nutrition. Typically, the term prebiotic refers to a material that stimulates the growth and/or activity of bacteria in the animals' digestive system resulting in beneficial health effects. Prebiotics may be selectively fermented ingredients that allow specific changes, both in the composition and/or activity of the gastrointestinal microflora, which confer health benefits upon the host. Probiotics generally refer to microorganisms that contribute to intestinal microbial balance which in turn play a role in maintaining health. Many species of lactic acid bacteria (LAB) such as, *Lactobacillus* and *Bifidobacterium* are generally considered as Probiotics, but some species of *Bacillus*, and some yeasts have also been found as suitable candidates. Postbiotics refer to non-viable bacterial products or metabolic byproducts from probiotic organisms that have biologic activity in the host.

The use of Probiotics to improve animal health and nutrition is well documented in the literature. In addition, prebiotics and postbiotics offer potential alternatives or adjunctive therapies to the use of live microorganisms. There is an increasing appreciation of the impact of pre-, pro-, and postbiotics on the modulation of the immune response, more specifically their role in modulating the expression of cytokines that regulate inflammatory responses at a local and systemic level. The ingestion of probiotic bacteria, for example, can potentially stabilize the immunologic barrier in the gut mucosa by reducing the generation of local pro-inflammatory cytokines. Alteration of the properties of the indigenous microflora by probiotic therapy was shown to reverse some immunologic disturbances in human's characteristic of Crohn's disease food allergy, and atopic eczema.[4, 7-10] Several probiotic species or their postbiotic products induce protective cytokines, including IL-10 and TGF-beta, and suppress pro-inflammatory cytokines, such as TNF, in the mucosa of healthy human patients, human patients with inflammatory bowel disease and mouse models.[1, 2, 11] It is presumed that comparable benefits would be realized in animals. Although there is suggestive evidence for each of these claims, the molecular details behind these mechanisms remain almost entirely undetermined. Not wishing to be bound by theory, it is believed that these mechanisms allow an animal being raised on feed containing pre-, pro- and post-biotics to divert energy away from maintaining a vigorous immune system and redirect it into growth and development.

Therefore there is considerable interest in including pre-, pro-, and post-biotic materials into animal feed. For example, Russian patent 2018313 discloses a powdered, spray-dried animal feed which is based upon milk and which contains certain bifidobacteria and streptococci. The animal feed is aimed primarily at livestock although it is mentioned that the feed may be fed to pets. Despite this growing interest on the benefits of various "biotoc" therapies, the beneficial effects of combined pre-, pro-, and postbiotic therapies on animal health and nutrition is not well documented. There remains an opportunity for compositions combining these therapies to provide a range of benefits both in the commercial livestock and companion pet care industries.

SUMMARY OF THE INVENTION

Animal feed compositions comprising a mixture of pre-, pro- and post-biotics, and methods of preparation, that are useful in overall health and nutrition as indicated by specific biochemical markers (e.g. blood sugar levels, lipid chemistry, liver function, full blood count, thyroid function, and inflammation markers such as ESR and C-reactive protein), gross physiological metrics (e.g. weight gain, percent mortality), and/or feed conversion rates.

In various aspects the invention provides animal feed compositions containing a mixture of microorganisms that are useful in promoting animal growth, health, and nutrition. The animal feed animal feed composition contains a mixture of a prebiotic; a probiotic bacteria comprising a mixture of *Lactobacillus* microorganisms produced by solid substrate and submerged liquid fermentation; a *Bacillus* probiotic bacteria produced by submerged liquid fermentation; a postbiotic derived from the liquid fermentation medium of the *lactobacillus* species; and a filler material.

The prebiotic is inulin, a fructo-oligosaccharide, or a gluco-oligosaccharide. The mixture of *Lactobacillus* includes *Pediococcus acidilactici, Pediococcus pentosaceus*, and *Lactobacillus plantarum*.

In some aspects the mixture of *Lactobacillus* is prepared by mixing a solid substrate fermentation of *Pediococcus acidilactici, Pediococcus pentosaceus*, and *Lactobacillus plantarum*; and the individual *Lactobacillus* species produced via submerged liquid fermentation wherein each of the 1 *Lactobacillus* bacteria are individually anaerobically fermented, harvested, dried, and ground to produce a powder having a mean particle size of 295 microns, with 60% of the mixture in the size range between 175-900 microns. Preferably the Lactobacilli from the solid substrate and liquid fermentations are mixed in equal proportion by weight.

In some aspects the a *Bacillus subtilis* has the 16S nucleic acid sequence of SEQ ID NO:1.

The postbiotic is prepared by collecting the supernatants from the centrifugation of each of the individual anaerobic fermentations of *Pediococcus acidilactici, Pediococcus pentosaceus*, and *Lactobacillus plantarum*; combing the supernatants obtained from step (a); freeze-drying the mixed supernatants to a moisture content less than about 5% by weight; and grinding the dried, mixed supernatants to a mean particle size of 295 microns, with 60% of the mixture in the size range between 175-900 microns.

The filler is for example rice, soy, or wheat bran, rice, soy, or wheat flour, corn meal, rye, barley, sorghum, dextrose, sucrose, fructose, maltodextrin, starch or any combination thereof.

The prebiotic, *lactobacillus* probiotic, and postbiotic components are combined in equal weight proportion. In other aspects the *bacillus* probiotic is mixed with the prebiotic, *lactobacillus* probiotic, and postbiotic mix at a ratio of from 1:1 to 1:20. The ratio of pre-, pro-, and postbiotic components to cereal grain filler ranges from about 1:1 to about 3:1. The final bacterial concentration is between about $10^6$ and $10^{11}$ colony forming units (cfu) per gram.

Also included in the invention is an animal feed composition coating 0.01 to 0.5% of the composition of the invention. In some aspects the pre-, pro-, postbiotic mixture is coated onto the feed particles using a wax, fat, sugar, or polysaccharide binder. Alternatively the pre-, pro-postbiotic mixture is integrated into a feed pellet, a mash feed or dissolved into the animals' drinking water supply. For example, the pre-, pro-, and postbiotic mixture is dosed into the water supply between about 0.1 and 1 kg per 1000 liters The invention further provides methods of improving the health and disease resistance of an animal by administering to an animal the animal feed, feed additive or supplement according to the invention. The method improves the health of an animal by increasing weight gain, reducing waste odor or increased utilization of feed proteins.

The animal is for example, shrimp, fin fish, poultry, swine, ruminants or companion pets.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

The invention provides compositions consisting of a mixture of specific pre-, pro-, and postbiotics for use as animal feed, feed additives or feed supplements. Unless stated otherwise, all percentages mentioned in this document are by weight based on the total weight of the composition.

The probiotic component of the composition comprises a mix of probiotic bacteria *Bacillus subtilis, Pediococcus acidilactici, Pediococcus pentosaceus*, and *Lactobacillus plantarum*. In preferred embodiments the compositions of the present invention comprise between 10-20% by weight of each of *Pediococcus acidilactici, Pediococcus pentosaceus*, and *Lactobacillus plantarum*, and from 1 to about 5 wt % of the *Bacillus subtilis*.

In preferred embodiments the *Bacillus subtilis* has an 16S sequence of:

(SEQ ID NO: 1)
```
AGCTCGGATCCACTAGTAACGGCCGCCAGTGTGCTGGAATTCGCCCTTAG

AAAGGAGGTGATCCAGCCGCACCTTCCGATACGGCTACCTTGTTACGACT

ACCGACTTCGGGTGTTACAAACTCTCGTGGTGTGACGGGCGGTGTGTACA

TCACCCCAATCATCTGTCCCACCTTCGGCGGCTGGCTCCATAAAGGTTAC

CTCAGGCCCGGGAACGTATTCACCGCGGCATGCTGATCCGCGATTACTAG

CGATTCCAGCTTCACGCAGTCGAGTTGCAGACTGCGATCCGAACTGAGAA

CAGATTTGTGRGATTGGCTTAACCTCGCGGTTTCGCTGCCCTTTGTTCTG

TCCATTGTAGCACGTGTGTAGCCCAGGTCATAAGGGGCATGATGATTTGA

CGTCATCCCCACCTTCCTCCGGTTTGTCACCGGCAGTCACCTTAGAGTGC

CCAACTGAATGCTGGCAACTAAGATCAAGGGTTGCGCTCGTTGCGGGACT

TAACCCAACATCTCACGACACGAGCTGACGACAACCATGCACCACCTGTC

ACTCTGCCCCCGAAGGGGACGTCCTATCTCTAGGATTGTCAGAGGATGTC

AAGACCTGGTAAGGTTCTTCGCGTTGCTTCGAATTAAACCACATGCTCCA

CCGCTTGTGCGGGCCCCCGTCAATTCCTTTGAGTTTCAGTCTTGCGACCG

TACTCCCCAGGCGGAGTGCTTAATGCGTTAGCTGCAGCACTAAAGGGGCG

GAAACCCCCTAACACTTAGCACTCATCGTTTACGGCGTGGACTACCAGGG

TATCTAATCCTGTTCGCTCCCCACGCTTTCGCTCCTCAGCGTCAGTTACA

GACCAGAGAGTCGCCTTCGCCACTGGTGTTCCTCCACATCTCTACGCATT

TCACCGCTACACGTGGAATTCCACTCTCCTCTTCTGCACTCAAGTTCCCC

AGTTTCCAATGACCCTCCCCGGTTGAGCCGGGGCTTTCACATCAGACTT

AAGAAACCGCCTGCGAGCCCTTTACGCCCAATAAtTCCGGACAACGCTTG

CCACCTACGTATTACCGCGGCTGCTGGCACGTAGTTAGCCGTGGCTTTCT

GGTTAGGTACCGTCAAGGTGCCGCCCTATTTGAACGGCACTTGTTCTTCC

CTAACAACAGAGCTTTACGATCCGAAAACCTTCATCACTCACGCGGCGTT

GCTCCGTCAGACTTTCGTCCATTGCGGAAGATTCCCTACTGCTGCCTCCC

GTAGGAGTCTGGGCCGTGTCTCAGTCCCAGTGTGGCCGATCACCCTCTCA

GGTCGGCTACGCATCGTCGCCTTGGTGAGCCGTTACCTCACCAACTAGCT

AATGCGCCGCGGGTCCATCTGTAAGTGGTAGCCGAAGCCACCTTTTATGT

CTGAACCATGCGGTTCAGACAACCATCCGGTATTAGCCCCGGTTTCCCGG

AGTTATCCCAGTCTTACAGGCAGGTTACCCACGTGTTACTCACCCGTCCG

CCGCTAACATCAGGGAGCAAGCTCCCATCTGTCCGCTCGACTTGCATGTA

TTAGGCACGCCGCCAGCGTTCGTCCTGAGCCATGAACAAACTCTAAGGGC

GAATTCTGCAGATATCCATCACACTGGCGGCCGCTCGAGCATGCATCTAG

AGGGCCCAATCGCCCTAT
```

The levels of the probiotic bacteria to be used according to the present invention will depend upon the types thereof. It is preferred that the present product contains probiotic bacteria in an amount between $10^5$ and $10^{11}$ colony forming units per gram. In a particularly preferred composition of the present invention the *lactobacillus* and *bacillus* organisms are present at a level of at least $1 \times 10^8$ cfu/g.

The term "probiotic bacteria" or "probiotics" as used herein, refers to microorganisms which when administered in adequate amounts confer a health or nutritional benefit. The probiotics according to the invention may be viable or non-viable. In case the probiotics are non-viable, they have to be substantially structurally intact, meaning that these non-viable micro-organisms are still sufficiently intact to avoid or delay disintegration in the distal intestinal tract thereby enabling the interaction of (conserved structures of) the non-viable micro-organisms with the immune system, particularly the mucosal immune system. The non-viable probiotics are metabolically-active. By "metabolically-active" is meant that they exhibit at least some residual enzyme activity characteristic to that type of probiotic.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfill the definition of "non-viable" (as given above) is considered to be "viable".

By the term "bioactive component" as used herein is meant a component which has a physiological effect upon the animal when consumed in adequate amounts.

In some embodiments of the invention, the probiotic bacteria employed are viable probiotic bacteria. The use of viable probiotic bacteria offers the advantage that these probiotic bacteria may become a part of the intestinal microflora, thereby providing additional health benefits.

The probiotic bacteria according to the invention may be produced using any standard fermentation process known in the art. For example, solid state or submerged liquid fermentation. The fermented cultures can be mixed cultures or single isolates.

The postbiotic components are derived from the fermentation supernatants remaining after centrifugation of the *lactobacillus* organisms and comprise from 5 to about 20% by weight of the composition.

The prebiotic component comprises gluco- and/or fructo-oligosaccharides (e.g. kestose, nystose, fructosylnystose, bifurcose, inulobiose, inulotriose, inulotetraose) including fermentation products resulting from the metabolism of inulin. In preferred embodiments the postbiotic components comprise between 0.1 and 10 wt % of the formula.

Additionally, the formulations may comprise up to about 50% by weight of a cereal grain filler such as Nutri-Sure™, dextrose, or other suitable filler material.

The compositions of the present invention are formulated for administration in animal feed, including mash and pellets, but may also be delivered via the drinking water supply. In one preferred embodiment the compositions have been formulated into feed mash. In another preferred embodiment the compositions have been formulated into a feed pellet. In yet another preferred embodiment the compositions can be directly formulated into an animals' drinking water supply. These compositions improve animal health, including accelerating weight gain, reducing the waste odor and/or increasing utilization of feed proteins.

When formulated for animal feed the compositions are typically dosed between 0.1 and 1 kg per metric ton of feed. Preferably, the feed composition is dosed at 50, 100, 200, 300, 400, 500, 600, 700, 800, 900 or more grams per metric ton of feed. When dosed into drinking water the compositions are typically dosed between 0.1 and 1 kg per 1000 liters. For aquatic applications, i.e., shrimp or fin fish, the compositions are typically dosed between 0.1 and 10 ppm. For example, for aquatic applications, the feed composition is dosed at 0.1, 0.2. 0.25, 0.5, 1, 1.5, 2, 2.5, 3, 3.5 4, 4.5, 5, 5.5 ppm. Preferably, the feed composition is dosed at 0.25 or 2.5 ppm.

In some aspects the, feed composition is added on top of a diet at about 0.05% to 5%. Preferably at 0.05, 0.1, 0.2, 0.3, 0.4, 0.5, 0.6, 0.7, 0.8, 0.9. 1.0. 2.0, 3.0, 4.0, or 5.0%

The pre-, pro- and postbiotic components of the compositions are preferably in powdered dried form; especially in spore form for those probiotic microorganisms which form spores.

The compositions according to the invention have been freeze dried to moisture content less than 20%, 15%, 10%, 9%, 8%, 7%, 6%, 5%, 4%, 3%, 2% or 1%. Preferably, the composition according to the invention has been freeze dried to moisture content less than 5%. In some embodiments the freeze dried powder is ground to decrease the particle size. For example the particle size is less than 1000, 900, 800, 700, 600, 500, 400, 300, 200 microns, or less. Preferably, the freeze dried powder is ground to decrease the particle size such that the particle size is less than 800 microns. In various embodiments the freeze dried powder is homogenized.

Further, if desired, the compositions may be encapsulated or agglomerated to further increase the probability of survival; for example in a wax matrix, sugar matrix, fat matrix or polysaccharide matrix.

The compositions of the invention are used to produce animal feed products and supplements or used as an animal feed additive. Although it is possible to achieve the benefits of the present invention by simply admixing the pre-, pro- and, and postbiotic compositions with animal feed or by using the compositions as a feed supplement, it is an object of the present invention to provide ready-to-eat feed products containing both a balanced diet ration and the composition of the present invention.

The feed supplement can be provided as a dried powder or liquid. Alternatively, the compositions of the invention may be formulated into "lick blocks".

The feed products can be produced by coating a pre-manufactured ready-to-eat animal feed product with the pre-, pro-, and postbiotic mixture. Coating the animal feed product can be achieved by methods known in the art. For example, the dried compositions of the invention can be dispersed in low melting grease or wax to which an animal feed product is added, or alternatively the molten grease or wax containing the pre-, pro-, and postbiotic mixture is sprayed onto the animal feed product.

Additionally, feed products containing the compositions of the invention may be prepared by mixing the pre-, pro-, and postbiotic composition with any suitable ingredients, such as those commonly used in the production of animal feed. The animal feed then may be produced in many different ways as desired. However, an especially suitable way to produce the feed products of the invention is by extrusion cooking. This can be done by methods well known in the art.

For example, in one suitable process, a feed mixture is fed into a preconditioner. The teed mixture is made up of a starch source and other ingredients such as sugar, salt, spices, seasonings, vitamins, minerals, flavoring agents, coloring agents, antioxidants, protein sources, yeast extracts, fats and the like.

Suitable starch sources are, for example, corn, rice, wheat, beets, barley, algae, soy and oats. The starch source may be a grain, a meal, a gluten or a flour.

Suitable protein sources may be selected from any suitable animal or vegetable protein source; for example meat meal, bone meal, fish meal, soy protein concentrates, milk proteins, gluten, yeast extracts, whey, and the like. The choice of the protein source will be largely determined by the nutritional needs, palatability considerations, and the type of feed product produced. Of course, the starch source may also be a source of protein.

If desired, sources of insoluble fiber may also be included; for example wheat bran, corn bran, rice bran, rye bran and the like. Further, if desired, a source of soluble fiber may be included, for example, chicory fibers, oat bran concentrate, guar gum, carob bean gum, xantham gum, and the like.

Depending upon the desired form of the feed product, the starch content of the feed mixture may be varied. For example, for an expanded cereal product, the feed mixture preferably includes up to about 40% by weight of starch. However, for a flaked product, it is not necessary to use large amounts of starch in the feed mixture since it is possible to flake an unexpanded product.

In the preconditioner, water or steam, or both, is mixed into the feed mixture. Sufficient water or steam is mixed into the feed mixture to moisten the feed mixture. If desired, the temperature of the feed mixture may be raised in the preconditioner to about 60-90° C. It is not necessary to subject the feed mixture to preconditioning but it is advantageous to do so.

The moistened feed leaving the preconditioner is then fed into an extruder along with the pre-, pro-, and post biotic composition. The extruder may be any suitable single or twin screw, cooking-extruder. Suitable extruders may be obtained from Wenger Manufacturing Inc, dextral SA, Buhler AG, and the like. During passage through the extruder, the moistened feed passes through a cooking zone, in which it is subjected to mechanical shear and is heated; for example up to a maximum temperature of up to about 150° C. and a forming zone. The gauge pressure of the forming zone is about 300 kPa to about 10 MPa, as desired. If desired, water or steam, or both, may be introduced into the cooking zone. If desired, a small amount of edible oil may be fed into the extruder along with the moistened feed to facilitate the extrusion process or as a carrier for oil soluble additives. Any suitable oil may be used; for example vegetable oils such as sunflower oil, safflower oil, corn oil, and the like. If oils are used, oils which are high in mono-unsaturates are particularly preferred. Hydrogenated oils or fats are also preferred. The amount of oil used is preferably kept below about 1% by weight.

The food matrix leaving the extruder is forced through a suitable die. A shaped extrudate, which has a cross-sectional shape corresponding to that of the orifice of the die, leaves the die.

If a flaked product is to be produced, the pieces may then be transferred to a flaking apparatus. Suitable apparatus are well known and widely used in the cereal industry and may be purchased from, for example, Buhler AG in Switzerland. If desired, the pieces may be partially dried before flaking.

The pieces are then dried to a moisture content below about 10% by weight. This is conveniently carried out in a hot air drier as is conventional.

The dried, ready-to-feed product contains about $10^5$ to about $10^{11}$ colony forming units (CFU) per gram (g) of the dried feed product; preferably about $10^6$ to about $10^9$ CFU/g. The dried feed product may contain from 0.01 to 0.5% by weight of the pre-, pro-, and post biotic mixture.

Numerous modifications may be made to the embodiments described above. For example, it is not necessary to produce the cereal product by extrusion cooking, Instead the cereal product may be produced by any suitable method of producing dried, ready-to-eat cereal pieces. For example, the feed materials may be cooked with water to provide a cooked paste. The paste is then roller-dried to produce dried flakes; usually of a thickness of about 0.6 to about 1 mm.

A better understanding of the present invention may be given with the following examples which are set forth to illustrate, but are not to be construed to limit the present invention.

EXAMPLES

Example 1: Preparation of the Composition

The composition of the present invention is prepared via a combination of submerged liquid fermentations and solid substrate fermentations.

Premix A: Solid Substrate Fermentation of *Lactobacillus*:

Individual purified isolates of *Pediococcus acidilactici*, *Pediococcus pentosaceus* and *Lactobacillus plantarum* were grown-up in separate fermenters using standard anaerobic submerged liquid fermentation protocols. The individual organisms were recovered from the fermenters via centrifugation, mixed together in equal proportions on a weight basis, then added to the following mixture: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. This mixture was allowed to ferment for up to 5 days at 30° C. Upon completion of the fermentation, the entire mixture was freeze dried to a moisture content less than 5%, ground to an average particle size of 295 microns, with 60% of the product in the size range between 175-840 microns, and homogenized. The final microbial concentration of the powdered product is between 109 and 1011 CFU/g.

Premix B: Submerged Fermentation of *Lactobacillus*:

Individual, purified isolates of *Pediococcus acidilactici*, *Pediococcus pentosaceus*, and *Lactobacillus plantarum* were grown-up in separate fermenters in the presence of inulin using standard anaerobic submerged liquid fermentation protocols. After fermentation the individual cultures were filtered, centrifuged, freeze dried to a moisture level less than about 5%, then ground to a mean particle size of 295 microns, with 60% of the product in the size range between 175-840 microns, and homogenized. The final microbial concentration of the powdered product is between 109 and 1011 CFU/g.

Premix C: Fermentation Supernatant:

The supernatants remaining after centrifugation of the organisms produced from the submerged fermentations of Premix B above were collected, mixed together, freeze dried to a moisture level less than about 5%, then ground to a mean particle size of 295 microns, with 60% of the product in the size range between 175-840 microns, and homogenized.

Premix D: Submerged Fermentation of *Bacillus*:

A sample of *Bacillus subtilis* (34KLB) is added to a 250 ml Erlenmeyer flask which also contains a sterilized solution of 100 mls distilled, deionized water, 2 grams Nutrient Broth, 2 grams AmberFerm (yeast extract) and 4 grams Maltodextrin. The flask is sealed and placed on an orbital shaker at 30° C. The culture is allowed to grow for 3-5 days.

A larger culture is prepared by adding 18 grams Nutrient Broth, 18 grams AmberFerm, and 36 grams Maltodextrin to a 1 liter flask with 900 mls distilled, deionized water. The flasks are sealed and sterilized as above. After cooling, 100 mls of the microbial media from the 250 ml Erlenmeyer flasks are added. The 1 liter flask is sealed, placed on an orbital shaker, and allowed to grow out for another 3-5 days at 30° C.

In the final grow-out phase before introduction to the fermenter, the culture from the 1 liter flask is transferred under sterile conditions to a sterilized 6 liter vessel and fermentation continues at 30° C. with aeration until stationary phase is achieved. The contents of the 6 liter culture flask is transferred to a fermenter which is also charged with a sterilized growth media made from 1 part yeast extract and 2 parts dextrose. The fermenter is run under aerobic conditions at pH 7.0 and 35° C. until cell density reaches $10^{11}$ CFU/ml.

For a dried product the fermenter is emptied through a filter, centrifuged, and the cell mass recovered. The cell mass is vacuum dried until moisture levels drop below about 5%. The final microbial activity of the dried product is typically between about $10^8$ and $10^{11}$ CFU/g.

A final composition is prepared by combining premixes A, B, and C in equal proportion by weight and mixing to homogeneity then mixing in Premix D and a filler. Typically, the final pre-, pro-, and postbiotic composition comprises 50% by weight of the combined Premixes A, B, and C, 3.33% by weight of Premix D, and 46.67% by weight Nutri-Sure™. The final activity of the *lactobacillus* in this formulation is 6.9×109 cfu/g and that of the *bacillus* is 3.7×108 cfu/g.

Example 2: Formulation of Animal Feed Products—Coating

The mixture from Example 1 is formulated onto animal feed pellets (shrimp, poultry, swine, and cattle) via the following methods:

A. 1 kilogram of a low melting grease (e.g. hydrogenated soybean oil with m.p. of 47-48° C.) is heated to just slightly above the melting point (50° C.). Once all the grease is melted, 1 kilogram of the dried, powdered composition from Example 1 is dispersed in the melt with rapid stirring, 999 kilograms of animal feed pellets are then quickly added to this melt and rapidly stirred to achieve homogeneous coating. The pellets are allowed to air dry overnight at room temperature. The final microbial activity of the coated pellet is between $10^7$ and $10^9$ CFU/g.

B. Alternatively, a low melting grease (e.g. hydrogenated soybean oil with m.p. of 47-48° C.) is added to a tank and heated to 50° C. with stirring. The melted grease is sprayed onto a stirred bed of feed pellets heated with forced air to about 45° C. The final weight of grease ranges from 1 to 5% w/w. The dried composition from Example 1 is added to the coated feed at weight between 0.01 and 1% w/w, the heated air flow is turned off, and the bed allowed to mix and cool until it reaches ambient temperature.

C. 1 kilogram of the dried, powdered composition from Example 1 is dispersed with vigorous mixing into 10 kilograms of sardine oil. While continuing to stir, this mixture is sprayed, at a rate of 1 kg/minute, onto a bed of feed pellets mixing in a ribbon blender operating at 60 hertz, in order to achieve a final loading of 1% w/w.

Example 3: Formulation of Animal Feed Products—Extrusion

The following dry mix composition is prepared:

| Ingredient | Level in Dry Mix (%) |
| --- | --- |
| Ground Corn (200 micron) | 64.0 |
| Ground Soybean Meal (200 micron) | 29.5 | mixed with sufficient water to make a 100% composition and subjected to high temperature (120-150° C.) with mixing for 20 minutes. During this process fat (2.6% w/w) may be added to the mixture. After cooking the mixture is conveyed into a Wenger TX52 Twin Screw extruder with the screws setup in a conveying configuration (low shear, low friction) and water is added at the rate of 23.5 kg/hr. The powder composition from Example 1 is metered into the extruder via an AccuRate screw feed at a rate sufficient to achieve 0.1 wt % of the final composition. The paste that is created is pushed through a die having 3 mm openings. The extrudate is cut into 3 mm lengths using a four blade rotating knife. The resulting pellets are collected and conveyed through a forced air, convection drying oven at 35° C. until moisture levels are below 10%. The microbial activity of the final composition is between $10^6$-$10^8$ CFU/g.

Example 4: Shrimp Feed Trials

A 53-day shrimp feeding study was conducted at the Texas A&M AgriLife Marine culture laboratory in Port Arkansas, Tex. PL10 animals with a mean initial weight of 0.005 grams were divided equally among three treatment tanks:

Control (Sucrose Only)
0.25 ppm dose of the composition from Example 1
2.5 ppm dose of the composition from Example 1

Figure 1:
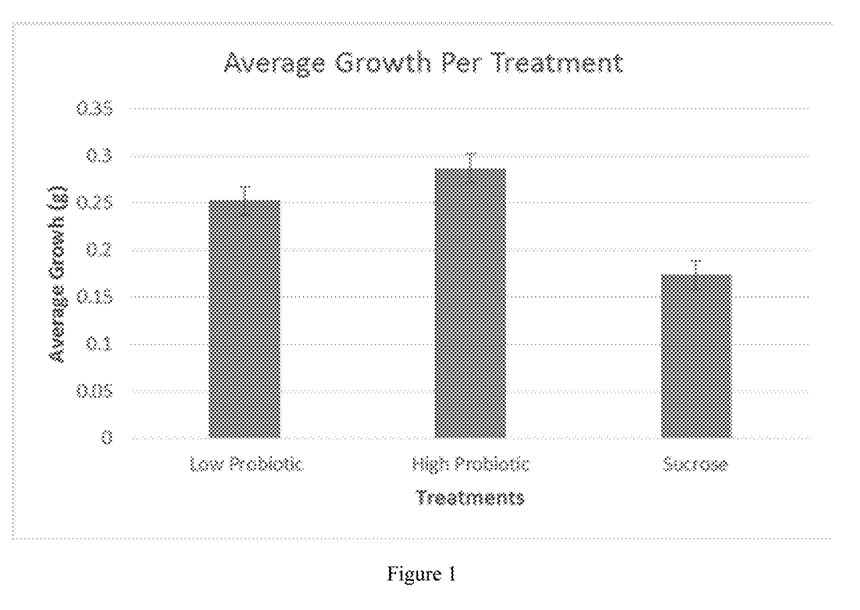
FIG. 1 shows the results for average growth per treatment.
Figure 2:
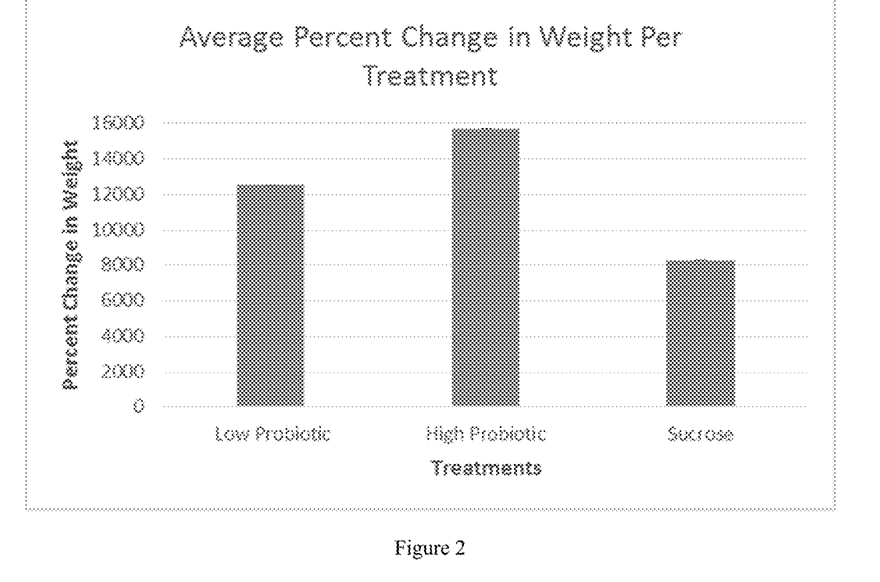
FIG. 2 shows the average change in weight per treatment.

Stocking density in each tank was 3384 shrimp/m².
All tanks were fed 40% protein diets based on a diminishing FCR through days 0-5. During days 0-3, in addition to the feed called for in the FCR, 9 g of 45% protein standard reference diet (SRD) were added daily. Feed protein rate and FCR were evaluated daily taking into consideration remaining feed in the tank, water quality, and biofloc level. The Example 1 composition was added daily as a liquid (dried composition dissolved in water) during the morning feeding. A zero water exchange raceway system was used. After 53 days the study was terminated and average shrimp weight in each tank determined. (FIG. 1 and FIG. 2).

Example 5: Poultry Feeding Study

Figure 3:
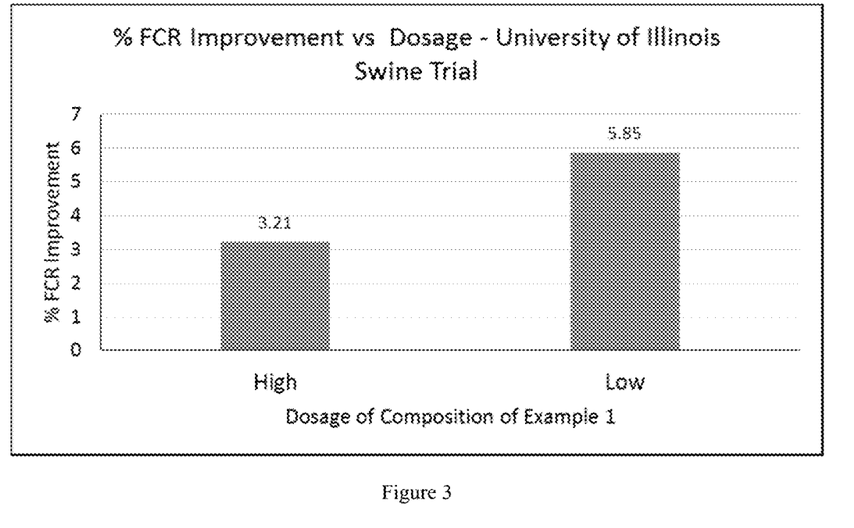
FIG. 3 shows the % FCR Improvement vs Dosage.

The study was carried out in an environmentally controlled poultry house. Birds were housed in pens (17 chicks/m²). Floor pens were assigned to six treatments:

1. Control Mash feed
2. Control Pellet Feed
3. 100 g Example 1 composition/ton Mash Feed
4. 1000 g Example 1 composition/ton Mash Feed
5. 100 g Example 1 composition/ton of Pellet Feed
6. 1000 g Example 1 composition/ton of Pellet Feed The distribution of experimental pens was arranged to avoid any effects from location in the poultry house. The pens had double wire netting between them to prevent physical contact between the birds in different pens, and to minimise the risk of cross contamination with *Bacillus* spores. The birds had free access to feed and water. Each pen was equipped with a hopper feeder to be manually filled on a daily basis. New wood shavings were used as litter. The initial brooding temperature was held at 31_C for the first three days, and then gradually lowered to 20_C by the end of the experiment. During the first two days of life, 24 h of light was provided, which was decreased to 22 h for the next 12 d, and to 20 h for the rest of the trial. Eimeria vaccination was carried out on the first day (by Coccivac spray in the hatchery) according to the instructions provided. The chickens were not vaccinated against other diseases. An antibiotic and coccidiostat-free basic diet was used during the experiment from 1 to 42 d. The ingredients (g/kg) were: maize 450, soyabean meal 48% 185 full fat soyabean 135, wheat 200 and a vitamin-mineral starter premix 30. Nutrient analyses (g/kg) were: crude protein 200; ether extract 72; crude fibre 41; ash 64; lysine 11_5; methionine 4_6; cystine 4_4. The composition of Example 1 was added to Mash and Pelleted Feeds at 100 g/t and 1000 g/t feed. All birds were weighed individually after their arrival from the hatchery and on d 7, 14, 21, 28, 35 and 42. Feed consumption was recorded on a pen basis at the same time as the live weight recording. Adjusted feed conversion ratio (FCR) results are shown in FIG. 3. The pelleted feed containing the composition of Example 1 showed significant improvement in FCR versus the controls.

Example 6: Poultry Feeding Study

The study was conducted in a cinder block structure with a clay floor. Continuous lighting was provided. Birds were housed in pens (27/pen) which provided a stocking density of 0.74 ft$^2$ per bird. Floor pens were assigned to six treatments (10 replicate pens per treatment):
1. Control mash feed
2. Control pellet feed
3. 50 grams of a 5% dose of composition 1/mt in mash feed
4. 500 grams of a 5% dose of composition 1/mt in mash feed
5. 500 grams of a 2% dose of composition 1/mt in pellet feed
6. 500 grams of a 4% dose of composition 1/mt in pellet feed New wood shavings were used on Day 0 and used litter was introduced in equal amounts per pen (4 lb./pen) on Day 4. The added litter at 4 days was homogenized prior to placement and contained enough levels of *E. coli*, *salmonella* and clostridia to allow for a mild challenge to naïve chickens. Prior to trial start, all pens were carefully inspected to ensure that there were no openings to allow for pen to pen migration by broilers. Chicks were given free access to food and water. Prior to placement and weighing on Day 0, birds were spray vaccinated for coccidiosis with Coccivac®-B. All pens were checked daily during the study. Observations included availability of feed and water, and brooder control for attainment of desired temperature. Feeds in mash form were fed on a schedule of Days 0-14, 15-28 and 29-42 of Starter, Grower and Finisher feeds respectively. Each feed type was prepared from a large basal diet as shown in Appendix A and were divided into aliquots and then blended with the test article followed by pelleting of 3 of the diets as indicated above.

APPENDIX A—FEED FORMULAS

| KEY | INGREDIENT | PERCENT | WEIGHT | COST | MIN | MAX |
|---|---|---|---|---|---|---|
| \multicolumn{7}{l}{4 Broiler Starter Feed 0-14 d Stored Jun. 18, 2014 14:02:23} |
| 159 | Corn, Yel 7.5% | 66.837 | 1336.74 | 164.29 | | |
| 201 | Soy Meal 47.9% | 22.885 | 457.69 | 600.00 | | |
| 239 | DDGS 27% HVA | 4.000 | 80.00 | 240.00 | 4.00 | 4.00 |
| 240 | M&B Ml 46% HVA | 4.000 | 80.00 | 585.00 | 4.00 | 4.00 |
| 500 | Limestone Fine | 0.473 | 9.45 | 50.86 | | |
| 502 | Dical 21/18.5% | 0.439 | 8.79 | 685.00 | | |
| 503 | Salt | 0.453 | 9.05 | 145.00 | | |
| 505 | Choline Cl 60% | 0.080 | 1.60 | 1240.00 | 0.08 | 0.08 |
| 527 | VDRp VitPremix | 0.040 | 0.80 | 3700.00 | 0.04 | 0.04 |
| 586 | VDRp TraMin Px | 0.085 | 1.70 | 1750.00 | 0.09 | 0.09 |
| 600 | L-Lysine HCl | 0.331 | 6.62 | 2220.00 | | 0.35 |
| 601 | DL-Meth 99% | 0.275 | 5.51 | 3954.00 | | 0.35 |
| 607 | L-Threonine98% | 0.084 | 1.69 | 2340.00 | | 0.11 |
| 614 | RonozymeP5000 | 0.018 | 0.36 | 1500.00 | 0.02 | 0.02 |
| | TOTALS | 100.000 | 2000.00 | 308.46 | 8.22 | |
| \multicolumn{7}{l}{Broiler Grower Feed 15-28 d Stored Jun. 18, 2014 14:02:50} |
| 159 | Corn, Yel 7.5% | 67.320 | 1346.40 | 164.29 | | |
| 201 | Soy Meal 47.9% | 18.273 | 365.46 | 600.00 | | |
| 239 | DDGS 27% HVA | 8.000 | 160.00 | 240.00 | 8.00 | 8.00 |
| 240 | M&B Ml 46% HVA | 4.000 | 80.00 | 585.00 | 4.00 | 4.00 |
| 405 | Soybean Oil | 0.415 | 8.30 | 780.00 | | |
| 500 | Limestone Fine | 0.446 | 8.92 | 50.86 | | |
| 502 | Dical 21/18.5% | 0.268 | 5.37 | 685.00 | | |
| 503 | Salt | 0.434 | 8.69 | 145.00 | | |
| 505 | Choline Cl 60% | 0.075 | 1.50 | 1240.00 | 0.08 | 0.08 |
| 527 | VDRp VitPremix | 0.040 | 0.80 | 3700.00 | 0.04 | 0.04 |
| 586 | VDRp TraMin Px | 0.085 | 1.70 | 1750.00 | 0.09 | 0.09 |
| 600 | L-Lysine HCl | 0.336 | 6.71 | 2220.00 | | 0.35 |
| 601 | DL-Meth 99% | 0.224 | 4.49 | 3954.00 | | 0.35 |
| 607 | L-Threonine98% | 0.066 | 1.31 | 2340.00 | | 0.08 |
| 614 | RonozymeP5000 | 0.018 | 0.36 | 1500.00 | 0.02 | 0.02 |
| | TOTALS | 100.000 | 2000.00 | 290.79 | 12.22 | |
| \multicolumn{7}{l}{Broiler Finisher Feed 29-42 d Stored Jun. 18, 2014 14:03:38} |
| 159 | Corn, Yel 7.5% | 65.984 | 1319.67 | 164.29 | | |
| 201 | Soy Meal 47.9% | 15.113 | 302.27 | 600.00 | | |
| 239 | DDGS 27% HVA | 12.000 | 240.00 | 240.00 | 12.00 | 12.00 |
| 240 | M&B Ml 46% HVA | 4.000 | 80.00 | 585.00 | 4.00 | 4.00 |
| 405 | Soybean Oil | 1.297 | 25.94 | 780.00 | | |
| 500 | Limestone Fine | 0.418 | 8.37 | 50.86 | | |
| 502 | Dical 21/18.5% | 0.087 | 1.74 | 685.00 | | |
| 503 | Salt | 0.417 | 8.33 | 145.00 | | |
| 505 | Choline Cl 60% | 0.075 | 1.50 | 1240.00 | 0.08 | 0.08 |
| 527 | VDRp VitPremix | 0.040 | 0.80 | 3700.00 | 0.04 | 0.04 |
| 586 | VDRp TraMin Px | 0.068 | 1.36 | 1750.00 | 0.07 | 0.07 |
| 600 | L-Lysine HCl | 0.295 | 5.90 | 2220.00 | | 0.35 |
| 601 | DL-Meth 99% | 0.157 | 3.14 | 3954.00 | | 0.35 |
| 607 | L-Threonine98% | 0.031 | 0.61 | 2340.00 | | 0.08 |
| 614 | RonozymeP5000 | 0.018 | 0.36 | 1500.00 | 0.02 | 0.02 |
| | TOTALS | 100.000 | 2000.00 | 280.17 | 16.20 | |

The composition of Example 1 was added to the mash and pelleted diets as mentioned above. All birds were weighed by pen on days 0, 35 and 42 and all pen feeds were weighed on days 14, 28 and 42. Day 42 Body Weight (BW) and Adjusted Feed Conversion Ratio (FCR) results are shown below. The pelleted feed containing composition Example 1 showed a 5.44% improvement in weight gain and a 3.2% improvement in FCR over the control diet.

| Treatment Group | D42 Body Wt (lb) | D42 FCR (lb/lb) |
|---|---|---|
| Control Pellet Diet | 4.408 | 1.866 |
| 500 g Exp. 1 in Pellet Diet | 4.648 | 1.807 |

Feed Conversion Ratio (FCR) is weight adjusted.

Example 7: Swine Feeding Study—USA

Procedures

A total of 144 weanling pigs (72 barrows, 72 gilts; 18-21 days of age) were obtained from the University of Illinois Imported Swine Research Laboratory. Two barrows and two gilts were allotted per pen and pigs had ad libitum access to feed and water throughout the trial. Pigs were blocked by body weight and ancestry at the time of weaning in a randomized complete block design. A standard three-phase feeding program was employed:

| Item, % | Phase 1 | Phase 2 | Phase 3 |
|---|---|---|---|
| Ground corn | 31.26 | 47.34 | 57.90 |
| Dried whey | 25.00 | 20.00 | 5.00 |
| Soybean meal | 20.24 | 23.69 | 31.18 |
| Lactose | 10.00 | — | — |
| Appetein | 7.50 | 3.00 | — |
| Choice white grease | 3.00 | 3.00 | 3.00 |
| Limestone | 1.14 | 1.09 | 0.90 |
| Dicalcium phosphate | 0.63 | 0.85 | 1.35 |
| Sodium chloride | 0.10 | 0.10 | — |
| Mineral premix | 0.35 | 0.35 | 0.35 |
| Vitamin premix | 0.20 | 0.20 | 0.20 |
| L-Lysine HCl | 0.04 | 0.05 | 0.02 |
| D,L-Methionine | 0.14 | 0.07 | 0.02 |
| Zinc Oxide | 0.40 | 0.26 | — |
| Copper sulfate | — | — | 0.08 |

The composition from Example 1 was added on top of each phased diet at either 0, 0.05, or 0.5% to produce three experimental dietary treatments. Phases 1 and 2 were each fed for 1-week and phase 3 diets were fed for the final 2 weeks of study.

There were 12 replicate pens for each of the 3 treatments, with each pen containing 4 pigs. Diets were formulated to meet or exceed the nutrient requirements for phase of growth based on NRC (2012).

Pigs and feed weights were recorded every week for 4-week period to determine body weight (BW), average daily gain (ADG) and average daily feed intake (ADFI) from which F:G was calculated per week and overall. Percent Feed conversion improvements versus the control leg are shown in FIG. 3.

Example 8: Swine Feeding Study—Thailand 8 pens in grower sheds housing 45 pigs per pen (360 total, 8 weeks of age, initial BW average=19.5 kg) were used in a 90-day growth experiment. Pigs were fed a typical mash diet containing the composition of Example 1 for the duration of the trial. Pigs were assigned to a completely randomized design with 45 pigs per pen and 4 replications. Treatments were:
1. Control (no added Biology)
2. Composition of Example 1 at 200 grams per ton of mash feed After 90 days, average daily body weight gain was 15% and the percent feed conversion improvement versus the control was 6.3%.

Example 9: Dairy Cattle Feeding Study

The composition of Example 1 was added to a liquid feed additive at the equivalent of 5% of the finished feed ration for 1200 head dairy cattle. The cattle were fed on this diet for a period of 30 days. Milk production was recorded for this time period and compared to the prior month. A 1.9% increase in milk production was observed and butterfat content increased 3.8% versus the prior month.

We claim:

1. An animal feed composition comprising a mixture of:
    a. a prebiotic selected from the group comprising inulin, fructo-, gluco-, or galcto-oligosaccharides;
    b. a probiotic bacteria comprising a mixture of *Lactobacillus* microorganisms produced by submerged liquid fermentation wherein the resulting organisms have been dried to a moisture content less than about 10% then ground to produce a powder having a mean particle size of less than about 800 microns;
    c. a *Bacillus* probiotic bacteria produced by submerged liquid fermentation wherein the resulting organism has been dried to a moisture content less than about 10% then ground to produce a powder having a mean particle size of less than about 800 microns;
    d. a postbiotic, wherein the postbiotic is dried liquid fermentation medium of the *Lactobacillus* microorganisms; and
    e. a filler material.

2. The composition of claim 1 wherein the mixture of *Lactobacillus* comprises *Pediococcus acidilactici*, *Pediococcus pentosaceus*, and *Lactobacillus plantarum*.

3. The composition of claim 2 wherein the mixture of *Lactobacillus* is prepared by mixing the individual *Lactobacillus* species produced via submerged liquid fermentation, wherein each of the *Lactobacillus* bacteria are individually anaerobically fermented to produce an individual anaerobic fermentation, harvested, dried, and ground to produce a powder having a mean particle size of 295 microns, with 60% of the mixture in the size range between 175-900 microns.

4. The composition of claim 1 wherein the *Bacillus* is a *Bacillus subtilis* having the 16S nucleic acid sequence of SEQ ID NO:1.

5. The composition of claim 3, wherein the postbiotic is prepared by:
    a. collecting the supernatants from the centrifugation of each of the individual anaerobic fermentations of *Pediococcus acidilactici, Pediococcus pentosaceus*, and *Lactobacillus plantarum;*
    b. combing the supernatants obtained from step (a);
    c. freeze-drying the mixed supernatants to a moisture content less than about 5% by weight; and
    d. grinding the dried, mixed supernatants to a mean particle size of 295 microns, with 60% of the mixture in the size range between 175-900 microns.

6. The composition of claim 1, wherein the filler comprises rice, soy, or wheat bran, rice, soy, or wheat flour, corn meal, rye, barley, sorghum, dextrose, sucrose, fructose, maltodextrin, starch or any combination thereof.

7. The composition of claim 1, wherein the prebiotic, lactobacillus probiotic, and postbiotic components are combined in equal weight proportion.

8. The composition of claim 7, wherein the *bacillus* probiotic is mixed with the prebiotic, *lactobacillus* probiotic, and postbiotic mix at a ratio of from 1:1 to 1:20.

9. The composition of claim 1, wherein the ratio of pre-, pro-, and postbiotic components to cereal grain filler ranges from about 1:1 to about 3:1.

10. The composition of claim 1, wherein the final bacterial concentration is between about $10^6$ and $10^{11}$ colony forming units (cfu) per gram.

11. An animal feed composition comprising 0.01 to 10.0% of the composition of claim 1.

12. An animal feed composition according to claim 11, wherein the pre-, pro-, postbiotic mixture is coated onto the feed particles using a wax, fat, sugar, oil or polysaccharide binder.

13. An animal feed composition according to claim 11, wherein the pre-, pro-postbiotic mixture is integrated into a feed pellet.

14. An animal feed composition according to claim 11, wherein the pre-, pro-, postbiotic mixture is integrated into a mash feed.

15. A process for dosing animals with the pre-, pro-, and postbiotic mixture of claim 1, wherein the mixture is dissolved into the animals' drinking water supply.

16. A process according to claim 15 wherein the pre-, pro-, and postbiotic mixture is dosed into the water supply between about 0.1 and 1 kg per 1000 liters.

17. A method of feeding an animal, the method comprising administering to the animal the animal feed composition according to any one of claims 1 to 14.

18. The method of claim 17, wherein the animal is shrimp, fin fish, poultry, swine, ruminants or companion pets.

* * * * *

SEQUENCE LISTING

<160> NUMBER OF SEQ ID NOS: 1

<210> SEQ ID NO 1
<211> LENGTH: 1668
<212> TYPE: DNA
<213> ORGANISM: Bacillus subtilis

<400> SEQUENCE: 1

```
agctcggatc cactagtaac ggccgccagt gtgctggaat tcgcccttag aaaggaggtg      60
atccagccgc accttccgat acggctacct tgttacgact tcacccaat catctgtccc      120 accttcggcg gctggctcca taaaggttac ctcaccgact tcgggtgtta caaactctcg      180
tggtgtgacg ggcggtgtgt acaaggcccg ggaacgtatt caccgcggca tgctgatccg      240
cgattactag cgattccagc ttcacgcagt cgagttgcag actgcgatcc gaactgagaa      300
cagatttgtg rgattggctt aacctcgcgg tttcgctgcc ctttgttctg tccattgtag      360
cacgtgtgta gcccaggtca taaggggcat gatgatttga cgtcatcccc accttcctcc      420
ggtttgtcac cggcagtcac cttagagtgc ccaactgaat gctggcaact aagatcaagg      480
gttgcgctcg ttgcgggact taacccaaca tctcacgaca cgagctgacg acaaccatgc      540
accacctgtc actctgcccc cgaaggggac gtcctatctc taggattgtc agaggatgtc      600
aagacctggt aaggttcttc gcgttgcttc gaattaaacc acatgctcca ccgcttgtgc      660
```

```
gggcccccgt caattcctttt gagtttcagt cttgcgaccg tactcccag gcggagtgct      720 taatgcgtta gctgcagcac taaaggggcg gaaaccccct aacacttagc actcatcgtt      780
tacggcgtgg actaccaggg tatctaatcc tgttcgctcc ccacgctttc gctcctcagc     840
gtcagttaca gaccagagag tcgccttcgc cactggtgtt cctccacatc tctacgcatt     900
tcaccgctac acgtggaatt ccactctcct cttctgcact caagttcccc agtttccaat     960
gaccctcccc ggttgagccg ggggctttca catcagactt aagaaaccgc ctgcgagccc    1020
tttacgccca ataattccgg acaacgcttg ccacctacgt attaccgcgg ctgctggcac    1080
gtagttagcc gtggctttct ggttaggtac cgtcaaggtg ccgccctatt tgaacggcac    1140
ttgttcttcc ctaacaacag agctttacga tccgaaaacc ttcatcactc acgcggcgtt    1200
gctccgtcag actttcgtcc attgcggaag attccctact gctgcctccc gtaggagtct    1260
gggccgtgtc tcagtcccag tgtggccgat caccctctca ggtcggctac gcatcgtcgc    1320
cttggtgagc cgttacctca ccaactagct aatgcgccgc gggtccatct gtaagtggta    1380
gccgaagcca ccttttatgt ctgaaccatg cggttcagac aaccatccgg tattagcccc    1440
ggtttcccgg agttatccca gtcttacagg caggttaccc acgtgttact cacccgtccg    1500
ccgctaacat cagggagcaa gctcccatct gtccgctcga cttgcatgta ttaggcacgc    1560
cgccagcgtt cgtcctgagc catgaacaaa ctctaagggc gaattctgca gatatccatc    1620
acactggcgg ccgctcgagc atgcatctag agggcccaat cgccctat                 1668
```

UNITED STATES PATENT AND TRADEMARK OFFICE
CERTIFICATE OF CORRECTION

PATENT NO. : 9,986,750 B2
APPLICATION NO. : 14/812598
DATED : June 5, 2018
INVENTOR(S) : Richard S. Carpenter et al.

It is certified that error appears in the above-identified patent and that said Letters Patent is hereby corrected as shown below:

In the Claims

At Column 16, Claim number 5, Line number 39, replace:
"combing the supernatants obtained from step (a);"
With:
--combining the supernatants obtained from step (a);--

At Column 16, Claim number 6, Line number 46, replace:
"prises rice, soy, or wheat bran, rice, soy, or wheat flour, corn"
With:
--prises rice, soy, wheat bran, wheat flour, corn--

At Column 16, Claim number 12, Line number 65, replace:
"wherein the pre-, pro-, postbiotic mixture is coated onto the"
With:
--wherein the pre-, pro-, postbiotic mixture is coated onto--

At Column 17, Claim number 13, Line number 2, replace:
"wherein the pre-, propostbiotic mixture is integrated into a"
With:
--wherein the pre-, pro-, postbiotic mixture is integrated into a--

Signed and Sealed this
Twenty-eighth Day of August, 2018

Andrei Iancu
*Director of the United States Patent and Trademark Office*